United States Patent [19]

Verhaag et al.

[11] Patent Number: 5,791,151
[45] Date of Patent: Aug. 11, 1998

[54] METHOD OF PRESERVING TISSUES AND ORGANS

[76] Inventors: Hubert Verhaag, Am Hagelkreuz 10, Kevelaer, Germany, 47623; Wilfried Schwörer, Rue Prinzipale 70, Artolsheim, France, 67390; Jürgen Schlegel, Hauptstrasse 9, Umkirch, Germany, 79224

[21] Appl. No.: 692,893

[22] Filed: Jul. 26, 1996

Related U.S. Application Data

[63] Continuation-in-part of Ser. No. 484,813, Jun. 7, 1995.

[30] Foreign Application Priority Data

Jul. 28, 1995 [DE] Germany .................. 195 27 734.1

[51] Int. Cl.[6] ............................................. F25D 25/00
[52] U.S. Cl. .................... 62/78; 62/62; 62/306; 62/371; 62/457.9; 435/1.1; 435/374; 426/312; 426/418
[58] Field of Search ............................. 62/62, 74, 78, 62/306, 371, 457.9; 435/1.1, 1.2, 1.3, 374; 426/312, 418

[56] References Cited

U.S. PATENT DOCUMENTS 2,402,199  6/1946  MacDonald .................. 426/418

*Primary Examiner*—Harold Joyce
*Assistant Examiner*—Pamela A. O'Connor
*Attorney, Agent, or Firm*—Townsend and Townsend and Crew

[57] ABSTRACT

A method is described for preserving tissues and organs, in particular of tissues and organs for transplantation, in which the tissue or organ to be treated is temporarily stored in a well-cooled state, in particular at a temperature in the range from −3° C. to 3° C., for a predeterminable time in an oxygen atmosphere, in a space which can be closed off in air tight manner, wherein the oxygen atmosphere is built up in the space which can be sealed off in air tight manner with a pressure which lies above the atmospheric pressure, and wherein the pressure in the closed space is kept at a pressure lying above the atmospheric pressure for the whole or the further period of intermediate storage.

15 Claims, 2 Drawing Sheets

METHOD OF PRESERVING TISSUES AND ORGANS

BACKGROUND OF THE INVENTION

This is a Continuation-In-Part Application of copending application Ser. No. 08/484,813, filed Jun. 21, 1995 for METHOD FOR PROCESSING FRESH MEAT.

SUMMARY OF THE INVENTION

The invention relates to a method or preserving tissues and organs, in particular of tissues and organs for transplantation.

With tissues and organs for transplatation the problem always exists that the transplantation must take place within a very short time, generally within a few hours after the removal of the tissue or organ from a body. An attempt is admittedly made to extend the time interval in which the tissue or organs can be transplanted into a new body by maintaining specific temperatures. However, this is only possible to an inadequate degree.

It is the object of the present invention to set forth a method by which tissue and organs, in particular tissues and organs for transplantation, can be preserved over a long period of time without their cell structure changing.

This object is satisfied in accordance with the invention essentially by a method in which the organs or tissues are temporarily stored in a well-cooled state, in particular at a temperature in the range from −3° C. to 3° C., for a predeterminable time in an oxygen atmosphere, in a space which can be closed off in air tight manner, wherein the oxygen atmosphere is built up in the space which can be sealed off in air tight manner with a pressure which lies above the atmospheric pressure, and wherein the pressure in the closed space is kept at a pressure lying above the atmospheric pressure for the whole of the further period of intermediate storage.

It has surprisingly been found that tissues and organs which are treated by this method do not have any changes in their cell structure, even several days after removal from a body, and are thus still suitable for a transplantation. The build-up of the oxygen atmosphere can take place in the method of the invention after the gas corresponding to the environmental or ambient atmosphere has been removed from the closeable space in a preceding step it is, however, also possible to blow oxygen directly with excess pressure into the space and to thereby displace the gas corresponding to the environmental atmosphere out of the space. It is important that an oxygen atmosphere is provided in some way or another in the closable space with a pressure which is elevated relative to the environment.

In this respect the oxygen atmosphere provided in the space should advantageously have a degree of purity of at least 50%, in particular of more than 80% a and preferably of at least 93%, whereby a situation is achieved in which an extremely pronounced preservation effect results for the treated tissue.

The method of the invention can be carried out particularly effectively when the evacuation process is carried out over a time interval of one hour, with the pressure within the closed space sinking to a depression of 50 to 100 mbar, and if the build-up of the oxygen atmosphere within the closed space then takes place to a pressure of 6 to 11 bar.

During the period of intermediate storage a continuous or discontinuous supplementation of the oxygen atmosphere in the closed space can be effected, with oxygen preferably being continuously introduced into the closed space at a pressure which is higher than a predeterminable discharge pressure so that a continuous through-flow sets in as a result of the pressure difference. Through this preferably continuous supplementation of the oxygen in the closed-off space the original oxygen content in the space can be maintained during the entire period of intermediate storage So that a particularly good preservation effect sets in.

Further Advantageous embodiments of the invention are evident from the subordinate claims. The invention will be explained in more detail by way of example in the following with reference to the drawings in which are shown.

DESCRIPTION OF THE PREFERRED EMBODIMENTS

Figure 1:
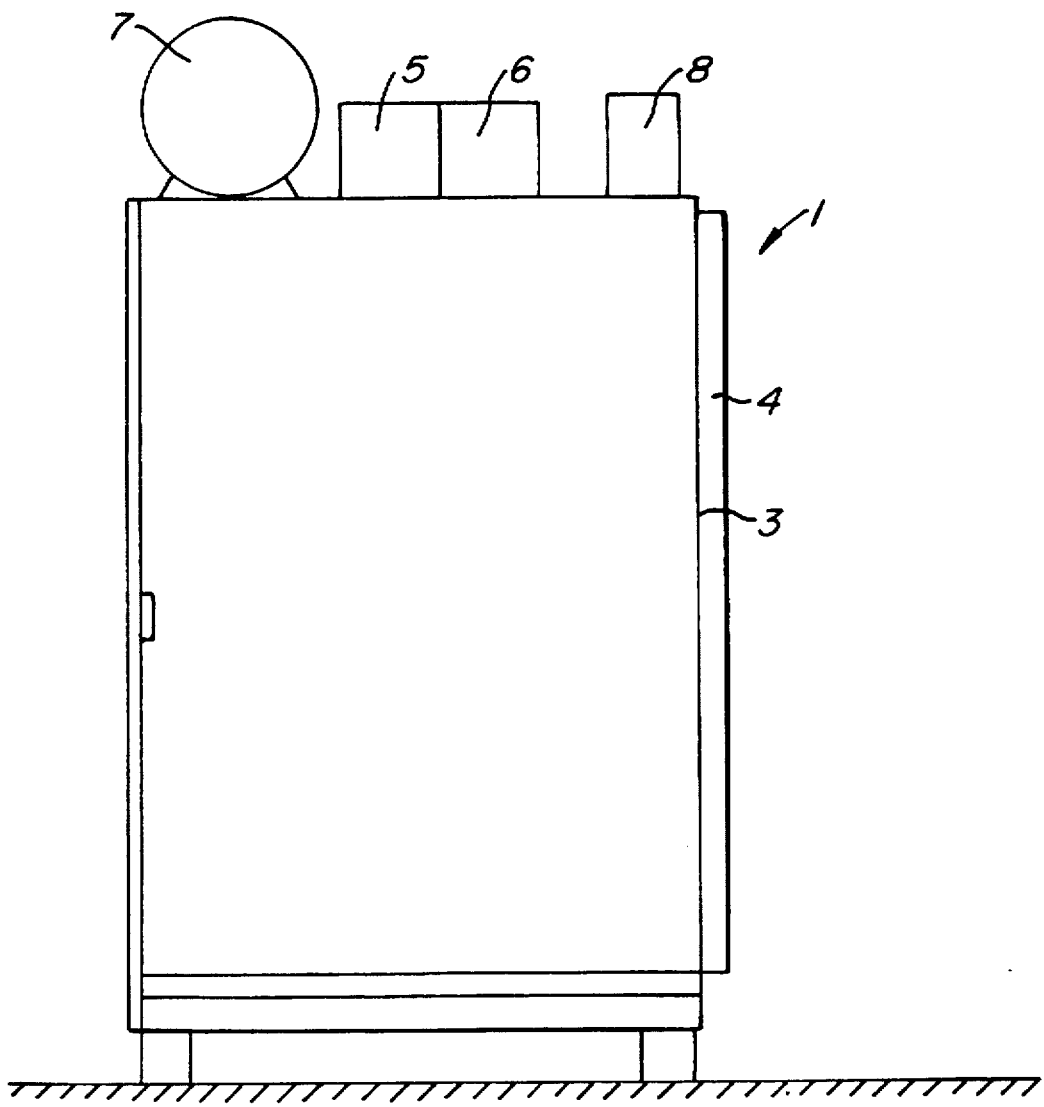
FIG. 1 is a schematic side-view of an apparatus for carrying out the method of the invention.

FIG. 1 shows an apparatus in accordance with the invention, with a housing of closed design consisting of a welded construction, having an opening 3 in order to place tissue or organs to be treated into the housing 1 in a manner such that oxygen has access to them from substantially on all sides. The opening 3 can be sealingly closed off by means of the housing door 4.

An oxygen generator 5, an evacuation pump 6 and also an oxygen tank 7 and an electronic control unit 8 are mounted on the housing 1.

Figure 2:
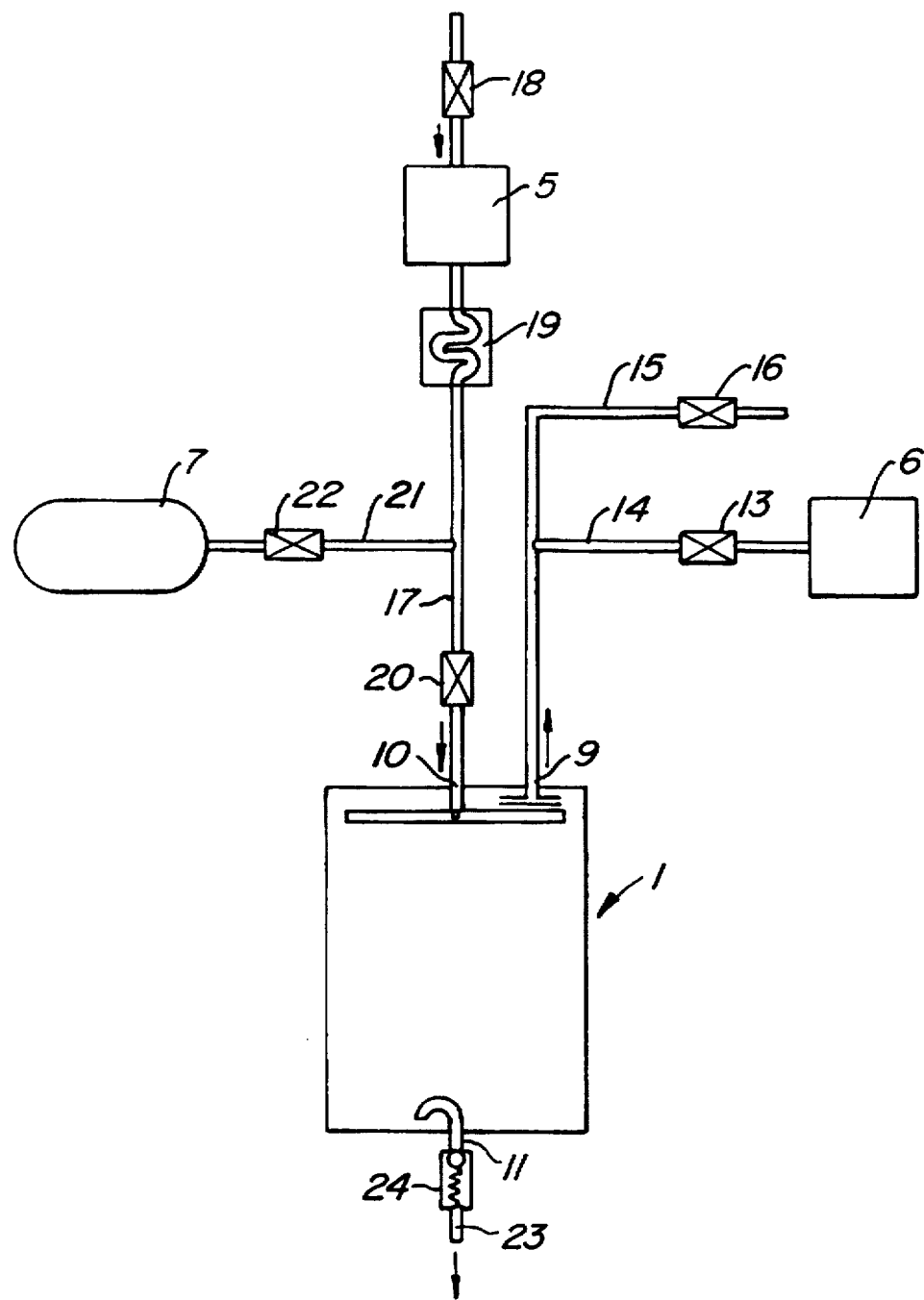
FIG. 2 is a schemdtic illustration to make clear the manner of operation of the apparatus for carrying the method of the invention.

The housing 1 furthermore has, as shown schematically in FIG. 2, an evacuation opening 9 and an oxygen inlet opening 10 at the roof side and also an oxygen extraction opening 11 at the floor Side.

The evacuation pump 6 is connected to the evacuation opening 9 via a pipe conduit or hose 14 closable by means of a solenoid valve 13.

A pipe conduit or a hose 15, which can likewise be closed by means of a solenoid valve 16, branches off from the pipe conduit 14 between the solenoid valve 13 and the evacuation opening 9 and opens into the environmental atmosphere.

The oxygen generator 5 is connected via a pipe conduit or a hose 17 to the inlet opening 10, with the suction end of the pipe conduit 14 being closable by means of a solenoid valve 18.

A heat exchanger 19 in the form or a Peltier element is furthermore provided between the oxygen generator 5 and the inlet opening 10. Here the temperature of the oxygen is measured and the oxygen is cooled down to a 0° C. The cooling of the oxygen contributes significantly to the preservation of the organs and tissues.

A solenoid valve 20 is furthermore provided between the oxygen generator 5 or the heat exchanger 19 and the inlet opening 10.

A further pipe conduit or a hose 21, which can be closed by a solenoid valve 22 and leads to the oxygen tank 7, branches off from the pipe conduit 17 between the solenoid valve 20 and the heat exchanger 19. The pipe conduit 17 terminates within the housing 1 in an oxygen distribution device.

The extraction of the oxygen from the inner space of the housing 1 takes place above a specific predeterminable pressure via a pipe conduit or a nose 23 which is closed below this presettable pressure by a pressure relief valve 24. The end of the pipe conduit 23 arranged within the housing 1 is turned back in an arc shape to the floor of the housing 1 in order to prevent the penetration of water or contamination.

This apparatus operates in the following way when carrying out the method of the invention:

After a tissue and organ to be treated has been laid into the housing 1 the housing door 4 is closed and locked. The control unit 8 now causes the filling of a non-illustrated pneumatic seal in the form of a hose which is laid in a closed path around the opening 3 with air at high pressure, whereby the diameter of the hose is broadened in order to seal off the doors 4 relative to the housing 1 in a gas and pressure tight manner.

In this initial state the solenoid valves 13, 16, 18, 20 and 21 are closed.

Thereafter the inner space of the housing is evacuated for approximately one hour, with the solenoid valve 13 being opened via the control unit 8. At the end of the one hour evacuation time a vacuum has almost been achieved within the housing 1, i.c. a depression of 50 to 100 mbar prevails.

Approximately two hours before the start of the evacuation of the housing 1 the generation of oxygen has already started via the oxygen generator 9, with the solenoid valves 18 and 22 being opened, the solenoid valve 20, however, still remains closed.

The oxygen thus flows after corresponding cleaning via a heat exchanger 19 and the pipe conduit 21 into the oxygen tank 7 in which an excess pressure of approximately 6 bar prevails at the end or the one hour evacuation period.

After approximately one hour the evacuation of the interior space of the housing is terminated and the solenoid valve 12 is closed. The solenoid valve 20 is now opened so that the oxygen standing under excess pressure can flow from the oxygen tank 7 into the inner space of the housing 1. After approximately five minutes a pressure equalisation takes place between the oxygen tank 7 and the inner space of the housing 1 and lies approximately at 0 to 0.6 bar excess pressure.

After the oxygen atmosphere within the housing 1 has been built up relatively rapidly, the solenoid valve 22 closes with pressure equalisation so that the oxygen from the oxygen generator 5 is directed via a direct route into the interior of the housing.

After a several hours an oxygen pressure of approximately 10 to 11 bar has been achieved in the interior space of the housing, at which the pressure relief valve 24 opens. From this point in time onward the oxygen flows continuously from the area of the inlet opening 10 to the discharge opening 11 so that the interior space of the housing is continuously flooded with fresh oxygen The oxygen in the closed-off space is brought to and kept at an excess pressure relative to the atmospheric pressure of 1 to 20 bar, and preferably of 6 to 11 bar during the period of intermediate storage. This state is retained until the end of the intermediate storage time which can last from several hours up to several days.

After the termination of the desired period of intermediate storage the oxygen generator 5 is switched off and the two solenoid valves 18 and 20 are closed. The solenoid valve 16 is opened for a few minutes in order to achieve a pressure equalisation between the interior space of the housing and the ambient atmosphere.

Prior to opening the door 4 of the housing the air is necessarily let out of the pneumatic door seal via a correspondingly controlled solenoid valve in order to avoid the door seal being damaged through the missing counter-pressure on opening the door.

What is claimed is:

1. Method of preserving tissues and organs for transplantation in intermediate storage comprising the steps of:

providing the tissues and organs for transplantation;

providing a space which can be closed off in air-tight manner;

storing the tissues and organs in a well-cooled state for a predetermined time in an oxygen atmosphere beginning at atmospheric pressure;

increasing pressure of the oxygen atmosphere in the space from atmospheric pressure to a pressure which lies between 6 and 20 bar above the atmospheric pressure; and, maintaining the pressure of the oxygen atmosphere in the space when closed off at a pressure between 6 and 20 bar above the atmospheric pressure for the intermediate storage.

2. The method of preserving tissues and organs for transplantation in intermediate storage according to claim 1 and comprising the further steps of:

extracting environmental atmosphere from the space when closed off before increasing the pressure of the oxygen atmosphere step.

3. The method of preserving tissues and organs for transplantation in intermediate storage according to claim 2 and wherein the storing the tissues and organs step includes:

extracting the environmental atmosphere is carried out during a time interval up to six hours, with the pressure in the space when closed off being reduced to a pressure which lies substantially beneath the atmospheric pressure.

4. The method of preserving tissues and organs for transplantation in intermediate storage according to claim 3 and comprising the further steps of:

the increasing pressure of the oxygen atmosphere step has an oxygen atmosphere with a degree of purity of at least 80%.

5. The method of preserving tissues and organs for transplantation in intermediate storage according to claim 3 and comprising the further steps of:

the increasing pressure of the oxygen atmosphere step has an oxygen atmosphere with a degree of purity of at least 93%.

6. The method of preserving tissues and organs for transplantation in intermediate storage according to claim 2 and comprising the further steps of:

the extracting the environmental atmosphere includes;
  initially evacuating with a steeper pressure reduction gradient in a first phase; and,
  finally evacuating with a lesser pressure reduction gradient in the last phase.

7. The method of preserving tissues and organs for transplantation in intermediate storage according to claim 6 and wherein the extracting the gas corresponding to the environmental atmosphere step includes:

extracting the environmental atmosphere over a time period of from one to three hours.

8. The method of preserving tissues and organs for transplantation in intermediate storage according to claim 6 and wherein the extracting the gas corresponding to the environmental atmosphere step includes:

extracting gas to generate a depression relative to atmospheric pressure of approximately 50 to 100 mbar.

9. The method of preserving tissues and organs for transplantation in intermediate storage according to claim 2 and comprising the further steps of:

generating oxygen before and/or during the extracting environmental atmosphere step;

storing the generated oxygen outside of the space in an oxygen tank at excess pressure; and, increasing pressure of the oxygen atmosphere in the space in an accelerated manner by means of the stored generated oxygen.

10. The method of preserving tissues and organs for transplantation in intermediate storage according to claim 9 and comprising the further steps of:

after increasing pressure of the oxygen atmosphere in the space in an accelerated manner by means of the stored generated oxygen.

generating oxygen required for the build-up of the excess pressure to the space when closed off directly.

11. The method of preserving tissues and organs for transplantation in intermediate storage according to claim 1 and comprising the further steps of:

the increasing pressure of the oxygen atmosphere step is provided by blowing oxygen under elevated pressure into the space when closed off.

12. The method of preserving tissues and organs for transplantation in intermediate storage according to claim 1 and comprising the further steps of:

the increasing pressure of the oxygen atmosphere step has an oxygen atmosphere with a degree of purity of at least 50%.

13. The method of preserving tissues and organs for transplantation in intermediate storage according to claim 1 and comprising the further steps of:

supplementing the oxygen atmosphere in the space when closed off with a continuous through-flow of oxygen.

14. The method of preserving tissues and organs for transplantation in intermediate storage according to claim 1 and comprising:

the maintaining the pressure of the oxygen atmosphere in the space when closed off for intermediate storage lies in a range from several hours to several days.

15. The method of preserving tissues and organs for transplantation in intermediate storage according to claim 1 and comprising:

storing the tissues and organs in a well-cooled state includes storing at a temperature in a range from −3° C. to 3° C.

* * * * *